United States Patent [19]

Turley

[11] Patent Number: 4,597,753
[45] Date of Patent: Jul. 1, 1986

[54] IMPLANTING METHOD AND DEVICE

[75] Inventor: Roger W. Turley, Haverhill, England

[73] Assignee: Hundon Forge Limited, Haverhill, England

[21] Appl. No.: 601,998

[22] Filed: Apr. 18, 1984

[30] Foreign Application Priority Data

Apr. 21, 1983 [GB] United Kingdom ............... 8310902
Aug. 4, 1983 [GB] United Kingdom ............... 8320993

[51] Int. Cl.$^4$ ............................................. A61M 5/18
[52] U.S. Cl. ........................................................ 604/61
[58] Field of Search .................... 604/60, 59, 61-64

[56] References Cited

U.S. PATENT DOCUMENTS 3,744,493 7/1973 Booher et al. ...................... 604/60
4,105,030 8/1978 Kercso ............................ 604/61 X
4,154,239 5/1979 Turley ............................... 604/61

Primary Examiner—Stephen C. Pellegrino
Attorney, Agent, or Firm—Gifford, Groh, VanOphem, Sheridan, Sprinkle & Dolgorukov

[57] ABSTRACT

An implanter for implanting treatment pellets beneath the skin of animals comprises a hollow needle (52) through which a drive pin (26) is displaceable to drive a pellet (64) through the needle and in use to a controlled depth below the skin. A forked abutment (54) straddles the needle, being spring urged into a normal location near the rear end of the needle. The abutment (54) is carried by a rearwardly extending rod (56) having a drive member (62) engagable by a thrust member (63) on the drive pin during part of the forward movement of the latter. In use, when the abutment member is against the animal being treated, the final part of the forward movement of the drive pin effects a retraction of the needle, leaving the pellet implanted at the correct depth (FIGS. 4 to 6).

9 Claims, 7 Drawing Figures

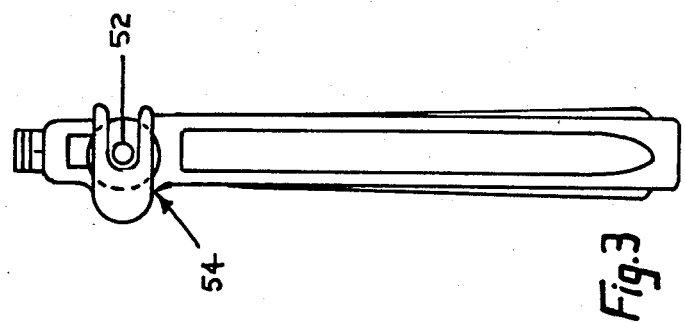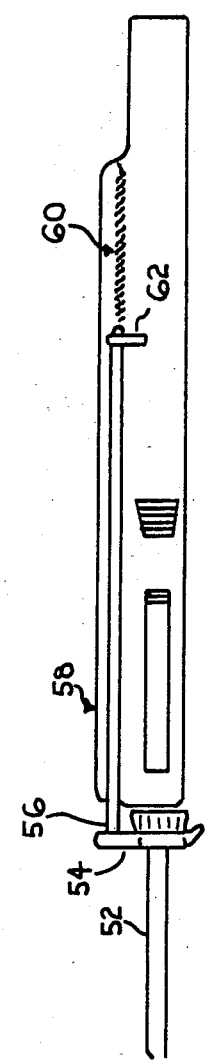

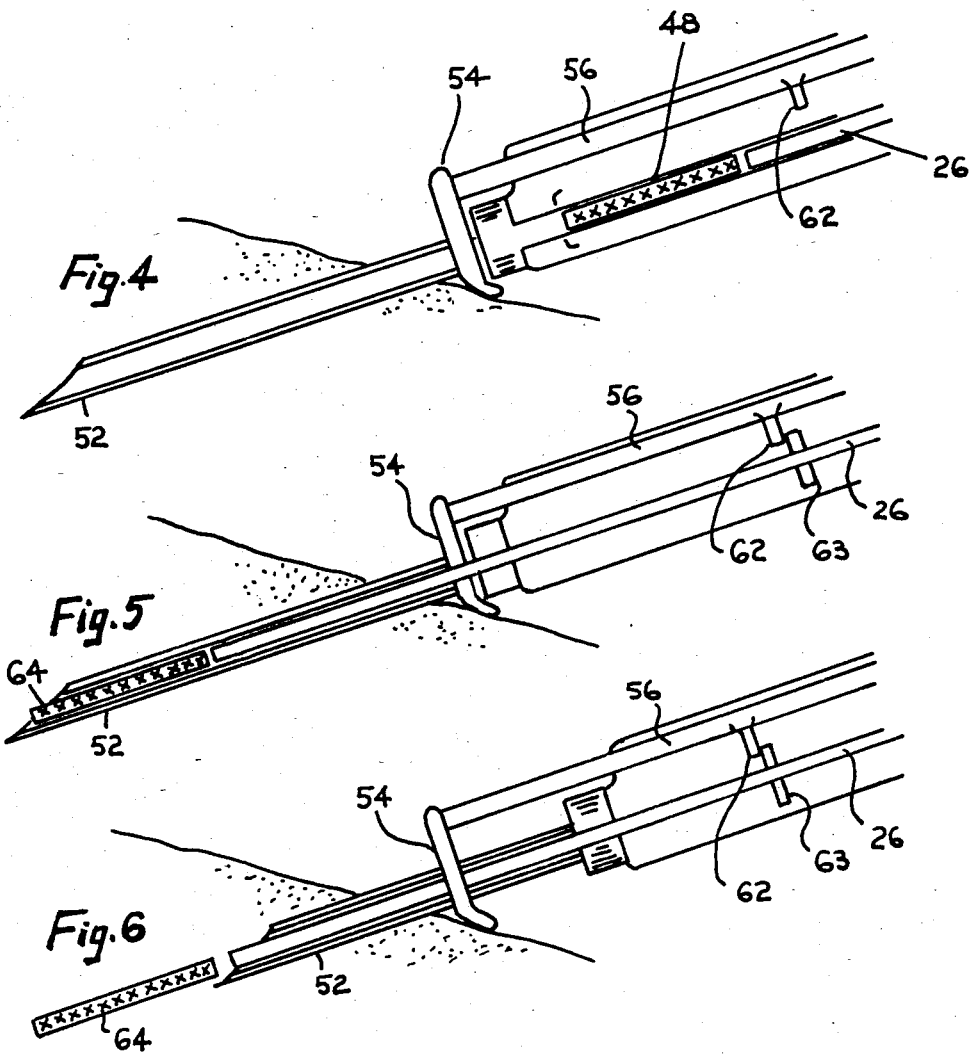

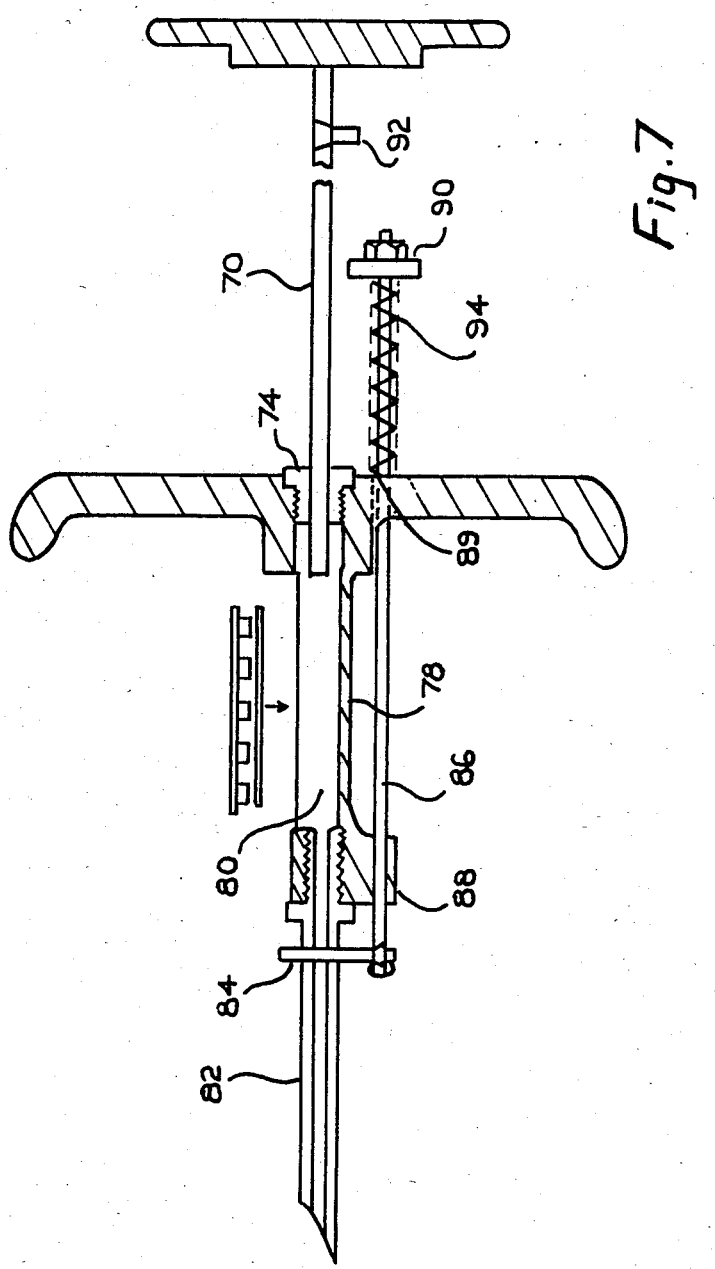

IMPLANTING METHOD AND DEVICE

DESCRIPTION

1. Field of Invention

This invention concerns an improved method and device for implanting pelletted drugs and other chemicals below the skin of an animal. The invention is particularly adaptable to hand-held implanter to facilitate the accurate location of one or more pellets below the skin.

2. Background to the Invention

It has been found that pelletted drugs and other chemical compounds will sometimes be rejected by an animal after implantation. Although all of the reasons for such rejection are not clearly established, it is clear that one of the contributory causes to a high rejection rate is placement of the pellet or pellets at an inadequate depth below the surface of the skin.

Clearly it is not desirable to inject the pellets too deeply into the animal since it is essential that the pellets are held in the fatty tissues adjacent the skin into which the chemical material and drugs will be absorbed. On the other hand, it is clear from observation that if the pellet or pellets are left just below the surface of the skin and effectively in the wound formed by the insertion of a hypodermic syringe needle, the pellet or pellets will be seen by the animal as a foreign body and will be rejected and the pellets will sometimes appear as a source of local infection and irritation to the animal before rejection.

It is an object of the present invention to provide an improved implanter to facilitate the implantation of pelletted materials at a correct depth below the surface of the skin so that an improvement can be obtained in the implant rejection rate which can otherwise arise.

THE INVENTION

According to the present invention, in an improved device for implanting pelletted material below the skin of an animal comprising:

1. an operating mechanism such as a gun-type body member including a trigger or a plunger-type mechanism;
2. a hollow needle protruding therefrom for insertion into the skin of an animal through which pelletted material can be forced; and
3. a pin adapted to be moved by the operating mechanism in a forward direction to urge pelletted material into the rear of the needle and through the same into the animal, and the improvement comprising:
   (1) an abutment member movable relative to the shank of the needle and normally located at or adjacent the junction of the needle and the operating mechanism and,
   (2) means for moving the said abutment member relative to the needle shank away from the said junction towards the tip of the needle in response to at least part of a forward movement of the implant pin to assist in the accurate placement of an implant relative to the surface of the skin.

Preferably the drive to the said abutment member is effected by means of a thrust member carried by the pin (or movable in response to movement of the pin) which in turn acts upon a member attached to the rear of the said abutment member to urge the abutment member in a forward direction.

By adjusting the position of the thrust member on, or relative to the motion of, the pin, the point at which the abutment member will begin to move can be controlled.

Preferably, means is provided for adjusting this parameter so that different sized implants cn be accommodated and/or different sized needles can be accommodated.

According to a preferred feature of the invention, the thrust member is adapted to engage the member protruding from the rear of the abutment at the point at which a pelletted implant just reaches the end of the needle.

In use, the device is held adjacent an animal's skin and the sharp end of the needle is forced into the skin until the abutment member at or adjacent the junction of the needle shank and operating mechanism just comes into contact with the skin. At that stage the operating mechanism is squeezed and the implanting pin is moved in a forward direction so as to urge the implant down the hollow interior of the needle. As the pelletted implant reaches the end of the needle and begins to enter the flesh of the animal, the thrust member associated with the pin makes contact with the member protruding from the rear of the said abutment which straddles the needle and continued squeezing movement of the operating mechanism will cause the needle attached to move in a rearward direction away from the abutment member. By keeping the abutment member in contact with the skin of the animal, the net effect is that the needle is withdrawn rearwardly leaving the pin at the same depth which, in turn, prevents the pelletted implant from being dragged back by the rearwardly moving needle. At the point of maximum travel of the operating machanism, the needle will have just cleared the rear end of the pelletted implant and withdrawal of the device in a rearward direction, pulling the needle out of the flesh, will leave the implant firmly embedded in the flesh at the desired depth.

Note that the depth at which the implant is left will be governed by the point at which the abutment begins to move the needle in a rearward direction with continued squeezing of the operating mechanism, provided the latter can accommodate a sufficient relative movement of pin and needle.

Preferably, spring means is provided urging the abutment in a rearward direction (i.e. towards the junction between the needle and the body of the operating member) so that when the trigger mechanism is released, the abutment moves back to its normal rest position.

In the same way, spring means is preferably provided to return the pin to its home position well clear and to the rear of the breech into which the implants are placed for injection, so that as soon as the operating mechanism is released, the pin will return to its home position.

The invention allows a relatively unskilled person to successfully and consistently implant drugs or like materials at a constant depth below the surface of the skin of an animal. The method is considerably simpler and more reliable than previous methods which have required the needle to be manually withdrawn while the operating mechanism is kept squeezed. In general, previous methods and devices have required a high degree of skill if the implant was not to be accidentally left too close to the surface of the skin at an insufficient depth thereby causing rejection or damage to the implant by crushing.

According to a preferred development of the invention, the needle mounting within a gun-shaped body member may itself be displacable rearwardly against return spring means so that, as the abutment is engaged by the thrust member of the advancing pin, the needle is automatically withdrawn in a rearward direction by continued squeezing action of the trigger mechanism without rearward movement of the gun-shaped body. This refinement clearly simplifies the action of implanting a pellet or pellets below the surface of the skin since the only skill required is to pierce the skin with the sharp end of the hollow needle and push the needle into the animal to the depth at which the abutment just makes contact with the skin whereafter a gentle squeezing action on the trigger mechanism will result in completely automatic disposal of the implant into the animal and withdrawal of the needle at least to the point at which the complete mechanism can be pulled out of the animal without any need for forward or rearward movement of the "gun" whatsoever.

The invention also lies in a method of implanting one or more pellets of a chemical such as a drug at a controlled depth below the skin of an animal comprising the steps of:

1. piercing the animal's skin with a hollow needle having a displacement abutment member associated therewith;
2. forcing by means of an advancing pin, the material to be implanted, through the hollow interior of the needle;
3. at or near the point at which the implant material is ejected from the hollow needle, effecting relative movement between the needle and an abutment member in contact with the surface of the animal's skin so that continued operation of the mechanism effecting forward movement of the implanting pin will effect withdrawal of the hollow needle around the pin if the abutment is kept in contact with the skin; and,
4. after the complete travel of the operating mechanism has been effected and the implant material is left fully clear of the rearwardly moving needle, removing the needle and pin from the animal.

Where the needle is rigidly attached to the body of the planting device, a rearward movement of the latter must be accommodated by the operator after the relative movement between the abutment and needle becomes effective.

Where relative movement between the needle and the body of the hand-held implanting device is permissible, no rearward movement of the device is necessary except to withdraw the needle at the end of the stroke and all of the movements to effect implantation are effected by the relative movements of the pin and needle and abutment.

The invention will now be described by way of reference to the accompanying drawings in which:

FIG. 2 is a top view of the implanter shown in FIG. 1;

FIG. 3 is a front view of the implanter in FIG. 1 looking from the left of the view shown in FIG. 1;

FIG. 4 illustrates to a larger scale the initial insertion of the needle into the flesh of an animal;

FIG. 5 is a similar view to that of FIG. 4 at an intermediate stage during the implanting process;

FIG. 6 illustrates the final stage of implantation just before the needle is withdrawn; and FIG. 7 illustrates an alternative construction of implanter incorporating the invention.

DETAILED DESCRIPTION OF THE DRAWINGS

Figure 1:
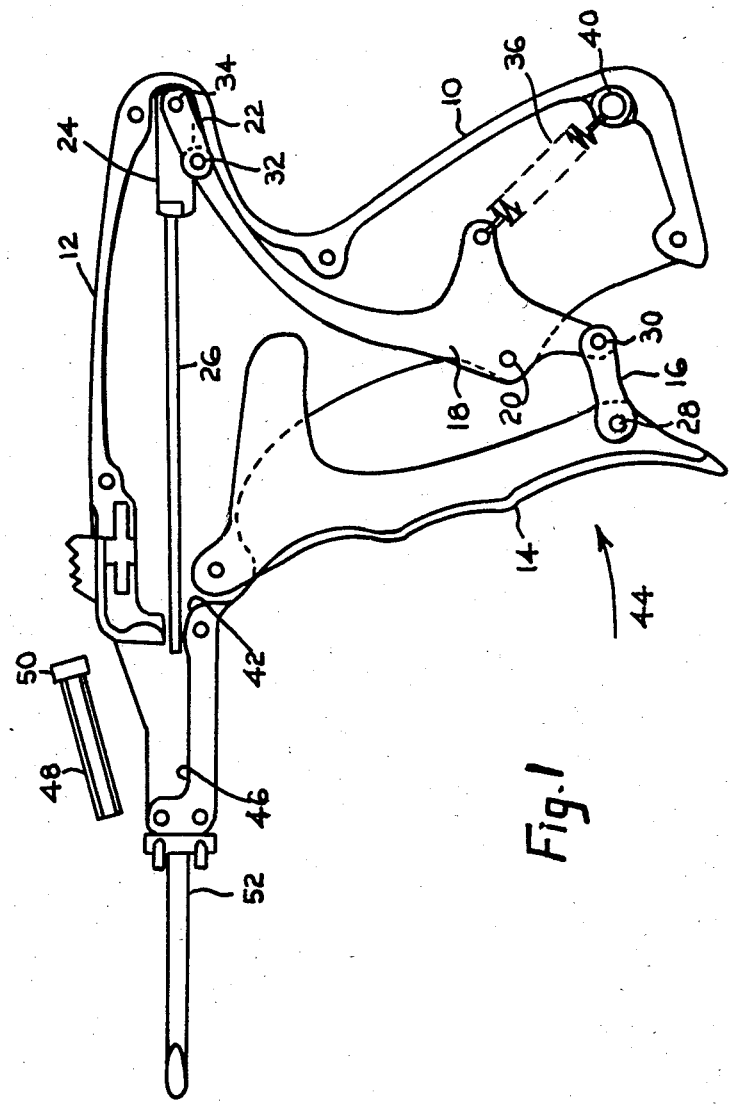
FIG. 1 is a side view of an implanter embodying the invention.

FIG. 1 shows an implant gun comprising handle 10 and body section 12 and hinged trigger 14. The latter acts on a pivoted mechanism made up of a short arm 16, a long arm 18 pivoted at 20, a second short arm 22 and a pin mount 24 from which an implanting pin 26 extends.

The short arms 16 and 22 are themselves pivoted to the trigger 14 at 28 and to the lower end of the long arm 18 at 30 and to the upper end of the long arm 18 at 32 and to the pin mount 24 at 34, respectively.

A spring 36 extends between a rearwardly extending protrusion of the long arm 18 and a fixing 40 at the lower rear of the handle 10.

A guide 42 is provided in the front end of the body 12 through which the forward end of the pin 26 just protrudes when the pin amount 24 is at the rear of the body 12.

A squeezing of the trigger 14 in the direction of the arrow 44 results in a forward movement of the pin 26.

In front of the body member 12 is a breech or implant chamber 46 into which cylindrical cartridges such as 48 containing one or more pellets 64 of drug or other chemical can be fitted so that the axis of the cylindrical cartridge such as 48 is aligned with the axis of the pin 26.

The implant cartridges are typically formed with an enlarged head at one end such as at 50 so as to prevent the cartridge from being inserted into the implant chamber 46 incorrectly.

The forward end of the implant chamber is an exit passage (not shown) which communicates with the interior of a hollow needle 52 through which the pellets 64 can be forced in advance of the pin 26 upon forward movement of the latter.

The stroke of the pin 26 is arranged to be such that the leading end of the pin can move from the rear of the breech 46 to the forward end of the needle 52.

As best seen in FIGS. 2 and 3, a bifurcated fork or abutment member 54 straddles the needle 52 and is mounted at the front end of a rod 56 which is guided in a lateral guide 58 on one side of the main body 12. Forward movement of the rod 56 results in corresponding forward movement of the fork 54.

The rod 56 is held urged in a rearward direction so that the forked abutment 54 sits snugly against the leading end of the body 12, by means of a spring 60 located at the end of the guide 58.

Forward movement of the forked abutment 54 is effected by a thrust member 62 which extends laterally from a point at or towards the rearward end of the rod 56 and is engagable by a thrust engaging member 63 (see FIG. 5) such as a disc or pin located near the rearward end of the pin 26. Relative positioning of the latter and/or the thrust member 62 along the length of the rod 56, controls the point at which the forked abutment member 54 will first be moved in a forward direction as the pin 26 is urged forwardly.

Forward movement of the rod 56 results in the spring 60 becoming stretched and the abutment member 54 and rod 56 will move in a rearward direction when the trigger 14 is released, under the restoring force of the stretched spring 60.

Although not shown, means is provided for adjusting the position of the thrust member 62 and the disc or other thrust engaging member 63 (Fig. 5) carried by or located on the pin 26.

It is to be understood that the pin mounting 24 may itself constitute or form a support for the thrust engaging member 63 for engaging the thrust member 62.

FIG. 3 shows how the bifurcated forked abutment member 54 straddles the needle 52.

FIGS. 4, 5 and 6 illustrate how the improvement operates in practice.

Initially, the gun is located with the sharp end of the needle against the skin of the animal with an implant cartridge 48 in position. The gun is moved swiftly in a forward direction piercing the skin so that the needle occupies the position shown in FIG. 4 with the forked abutment just touching the skin.

The trigger 14 is then squeezed until the intermediate position is reached at which the material which is to be implanted (shown as a single large pellet, but possibly made up of a number of pellets one behind the other) and designated by reference numeral 64, just reaches the end of the needle 52. At this point the abutment thrust engaging member 63 on the pin 26 (or the mount 24) just engages the thrust member 62. continued squeezing of the trigger 14 will effect relative movement of the abutment 54 and needle 52 and an effective withdrawal of the needle over the pin leaving the pellet 64 firmly embedded at controlled depth.

Although not shown, the needle may be mounted for movement relative to the gun so that the latter can be held stationary until the end.

FIG. 7 shows an alternative embodiment of pellet implanter having a plunger type operating mechanism.

A drive pin 70, terminated at the rear by a pressure plate 72 to be pressed by the palm of the hand, extends forwardly through a guide 74 in a finger grip 76. The latter is disposed at the rear end of a body 78 which has a pellet-cartridge-receiving chamber 80 behind a hollow needle 82.

By squeezing the palm plate 72 towards the finger grip 76, the rod can be displaced through the chamber 80 and into and through the needle 82, driving a pellet in front of it.

A forked abutment 84 is disposed around the needle 82 towards the rear end thereof, being carried at the front end of a rod 86 which extends rearwardly through a front guide 88 and a rear guide 89 carried by the finger grip 76. At its rear end, the rod 86 carries a drive member 90 engagable by a thrust member 92, such as a thrust ring, on the drive pin 70, thereby to enable pellet implantation i the manner previously described with reference to FIGS. 4 to 6.

A return spring 94 acts between the finger grip 76 and the rod drive member 90, thereby to urge the forked abutment 84 towards its normal position adjacent the rear end of the needle 82.

An implanter as illustrated in FIG. 7 may be fully machined or metal die cast, or it can be inexpensively moulded of plastics material for short-lived usage.

I claim:

1. A pellet implanter for the injection of animals, comprising:
a body member,
a hollow needle extending from one end of the body member,
a pin slidably received in the needle and forwardly movable through the needle to urge pelleted material through said needle and into the animal;
an operating mechanism for driving the pin, the mechanism carried by the body member,
abutment means movably mounted on the body member and located outside and adjacent to the needle, said abutment means being movable relative to the shank of the needle in the longitudinal direction thereof and normally being positioned remote from the needle tip; and
means establishing a coupling between the abutment means and the pin for moving the abutment means relative to the needle shank towards the needle tip in response to at least part of the forward movement of the pin.

2. An implanter according to claim 1, wherein the abutment means is movable by means of a thrust member drivable by the pin and which, during forward movement of the pin, is brought into engagement with a drive member coupled to the abutment means.

3. An implanter according to claim 1, wherein abutment means is spring urged rearwardly into its normal position remote from the needle tip.

4. An implanter according to claim 1 wherein the operating mechanism is spring loaded to urge the pin towards its rearmost position.

5. An implanter according to claim 1, including a breech chamber open or openable to receive a pellet when the pin is in its rearmost position.

6. An implanter according to claim 1, wherein the needle is carried by a mounting which is displacable rearwardly, against a return spring, relative to the operating mechanism.

7. An implanter according to claim 1, wherein the operating mechanism comprises a gun-like body including a trigger mechanism.

8. An implanter according to claim 1, wherein the operating mechanism comprises a syringe-type plunger carrying the pin.

9. A method of implanting pellets at a controlled depth below the skin of an animal, the method comprising the steps of:
(a) piercing the animal's skin with a hollow needle having a displacement abutment member associated therewith;
(b) forcing by means of an advancing pin, the material to be implanted, through the hollow interior of the needle after the latter has been pushed into the animal to a depth sufficient to bring the abutment member into contact with the skin;
(c) adjacent the point at which the implant material is ejected from the hollow needle, effecting relative movement between the needle and the abutment member in contact with the surface of the animal's skin so that continued operation of the mechanism effecting forward movement of the implanting pin will effect withdrawl of the hollow needle around the pin if the abutment is kept in contact with the skin; and
(d) after the complete travel of the operating mechanism has been effected and the implant material is left fully clear of the rearwardly moving needle, removing the needle and pin from the animal.

* * * * *